(12) United States Patent
Hall

(10) Patent No.: US 8,113,834 B2
(45) Date of Patent: Feb. 14, 2012

(54) ARRANGEMENT OF TWO OR MORE IMPLANTS PROVIDED WITH GROWTH-STIMULATING SUBSTANCE(S)

(75) Inventor: Jan Hall, Göteborg (SE)

(73) Assignee: Nobel Biocare AB (Publ), Gothenburg (SE)

( * ) Notice: Subject to any disclaimer, the term of this patent is extended or adjusted under 35 U.S.C. 154(b) by 133 days.

(21) Appl. No.: 12/126,542

(22) Filed: May 23, 2008

(65) Prior Publication Data

US 2008/0228279 A1  Sep. 18, 2008

Related U.S. Application Data

(62) Division of application No. 10/521,113, filed as application No. PCT/SE03/01109 on Jun. 26, 2003, now abandoned.

(30) Foreign Application Priority Data

Jul. 25, 2002 (SE) .................................. 0202318

(51) Int. Cl.
*A61C 8/00* (2006.01)
(52) U.S. Cl. .................................................. 433/173
(58) Field of Classification Search .......... 433/172, 433/173, 174, 215
See application file for complete search history.

(56) References Cited

U.S. PATENT DOCUMENTS

| 4,531,916 | A | | 7/1985 | Scantlebury et al. | |
|---|---|---|---|---|---|
| 5,683,249 | A | | 11/1997 | Ibsen et al. | |
| 5,700,479 | A | * | 12/1997 | Lundgren | 424/435 |
| 6,193,516 | B1 | * | 2/2001 | Story | 433/173 |
| 6,244,868 | B1 | * | 6/2001 | Schappert | 433/173 |
| 6,325,627 | B1 | * | 12/2001 | Ashman | 433/173 |
| 6,402,518 | B1 | * | 6/2002 | Ashman | 433/215 |
| 7,172,422 | B1 | | 2/2007 | Essigner | |

FOREIGN PATENT DOCUMENTS

| WO | WO-0072775 | 12/2000 |
|---|---|---|
| WO | WO-0072776 | 12/2000 |
| WO | WO-0072777 | 12/2000 |

OTHER PUBLICATIONS

International Search Report dated Oct. 7, 2003, Int'l Appl. No. PCT/SE2003/01109.

* cited by examiner

*Primary Examiner* — Ralph Lewis

(74) *Attorney, Agent, or Firm* — Connolly Bove Lodge & Hutz LLP

(57) ABSTRACT

Two or more implants (8, 9, 10) are arranged in succession in the jaw bone (1) and bear or comprise growth-stimulating substances (25), here called GSS, which, as a function of secretion of body fluid at the implants, are intended to be released and form new bone (11-15) around the implants. The implants are designed to work with a release process for GSS, permitting a leveling-out effect along the extent of the jaw bone in the horizontal and/or vertical direction and/or a level-raising effect in the vertical direction. In this way it is possible to achieve optimum positions for the implants without the risk of reduced stability and/or compromised esthetics.

10 Claims, 3 Drawing Sheets

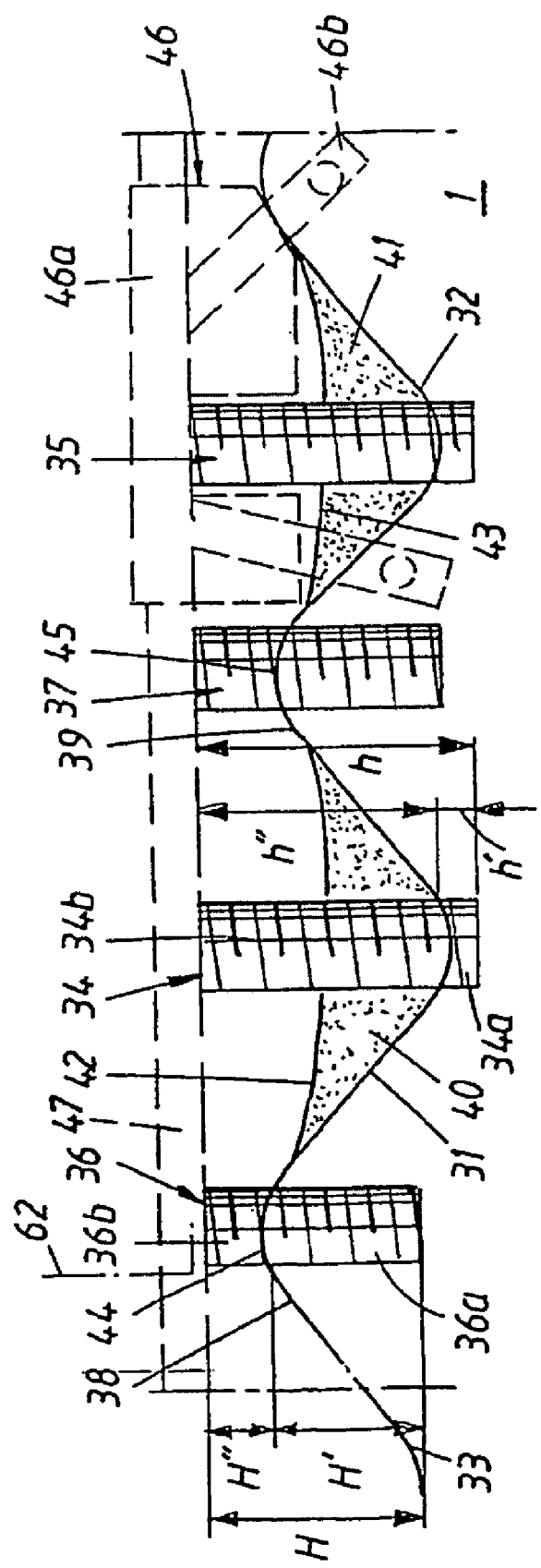

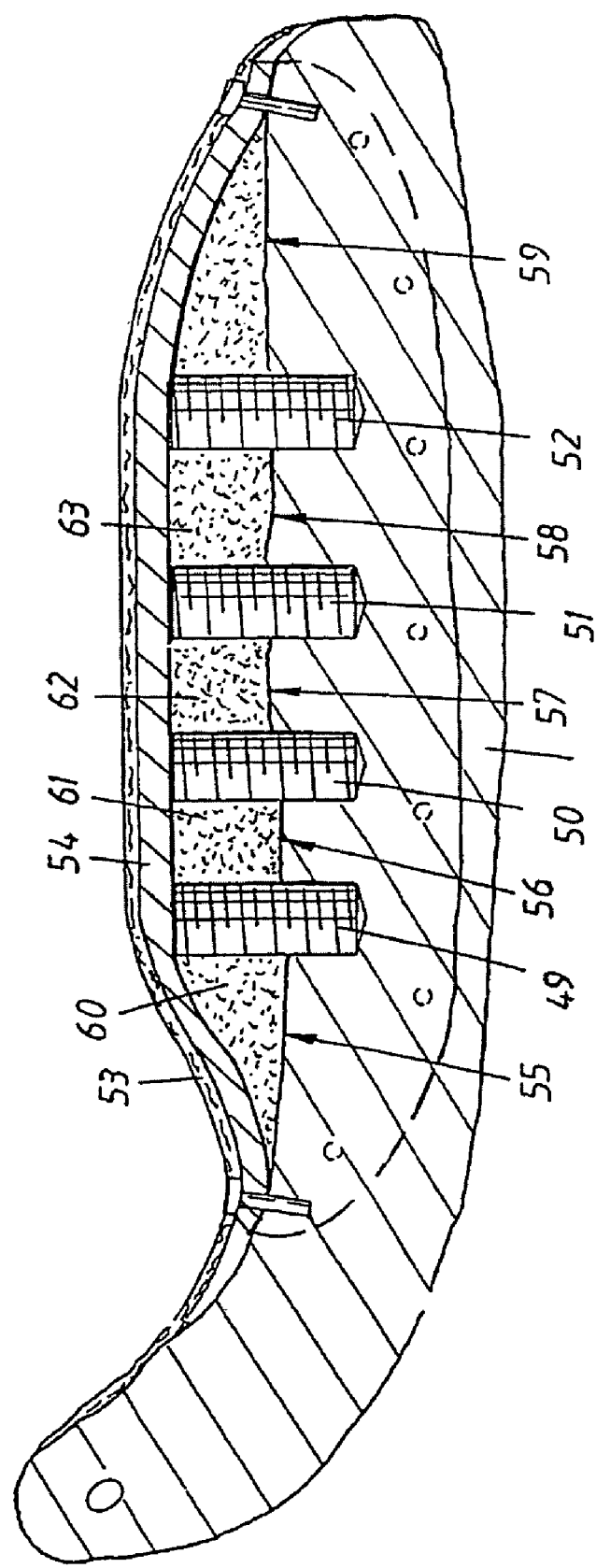

Figure 1:
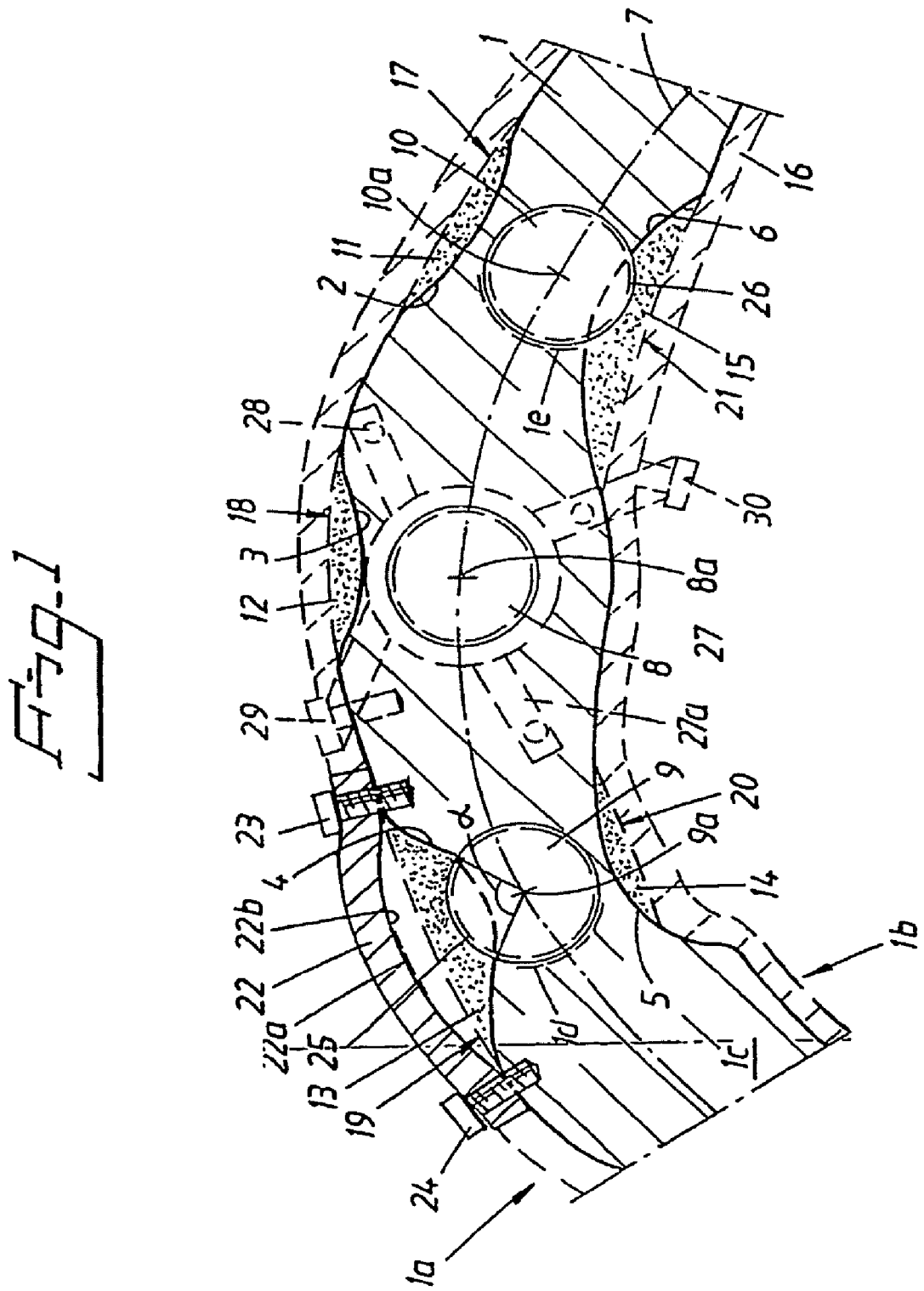

ARRANGEMENT OF TWO OR MORE IMPLANTS PROVIDED WITH GROWTH-STIMULATING SUBSTANCE(S)

CROSS-REFERENCE TO RELATED APPLICATIONS

This application is a Divisional Application of U.S. patent application Ser. No. 10/521,113, filed Jan. 12, 2005, which is a 35 U.S.C. 371 Application of International Application No. PCT/SE03/001109, filed Jun. 26, 2003, claiming priority of Swedish Application No. 0202318-2, filed Jul. 25, 2002, the entire disclosures of which are herein incorporated by reference in their entireties.

The present invention relates to an arrangement of two or more implants arranged in succession in the jaw bone and bearing or comprising growth-stimulating substance(s), here called GSS, which, as a function of secretion of body fluid at the implants, is/are intended to be released and form new bone around the implants.

It has been proposed that GSS be applied to implants so that, when the implants are in their positions fitted in the jaw bone holes, the GSS is released and builds up a new bone structure which is intended to increase the stability of the implant and/or optimize the appearance around the implant.

Reference may be made in this connection to patent applications SE 9901972-1 and WO 00/72778 filed by the same Applicant and inventor. Reference may also be made to the article published by, inter alia, the inventor of the present patent application and entitled "Properties of a New Porous Oxide Surface on Titanium Implants, Volume 1: The Oxidized Titanium Surface, Applied Osseointegration Research".

Examples of GSS which may be mentioned are matrix molecules, growth factors and differentiation factors and/or peptides with growth-stimulating properties.

In practical work on fitting implants in jaw bone, it has been proposed that the implants should be placed in the jaw bone at sites where the condition of the jaw bone in the initial stage is best or acceptable. In the case of completely or partially defective or irregular jaw bones, this has meant that the implant has been given a location which is not advantageous for the dental construction to be applied to the implant and which has a negative impact on the construction in question. In the worst cases, this can mean that the patient has to do without the desired dental construction. There is also a requirement that a degenerated jaw bone can be provided with implants used for supporting the dental construction. The present invention aims to solve these problems among others.

In connection with the function for forming new bone, problems may arise in obtaining the correct spatial distribution of newly formed bone in the jaw bone. According to the present invention, it is proposed that the jaw bone's soft tissue, with or without periosteum and/or a possible strengthening element, for example a polymer membrane, will protect the implant or implants during the formation of new bone. In this connection, problems may arise in correctly using the soft tissue and possible periosteum and/or strengthening element. The invention aims to solve these problems too.

There is therefore a need to be able to extend the choices available to the surgeon, dentist or other user with respect to the locations of the implants and of the jaw bone holes for these, despite the requirement that the stability of the implants must be maintained and that this stability must be comparable to that obtained in cases where the implant and associated hole are arranged in more solid jaw bone. In dental fixtures of the type in question, there is also a requirement to obtain a fixture which is of high quality from the point of view of appearance. The invention solves these problems too.

The feature which can principally be regarded as characterizing the invention is that the implants are designed to work with a release process for the growth-stimulating substance or substances GSS, permitting a leveling-out effect along the extent of the jaw bone in the horizontal and/or vertical direction and/or a level-raising effect in the vertical direction.

In further developments of the invention, the latter is intended to be able to function for jaw bones which have one or more recesses in the horizontal plane. One or more first implants can in this case be arranged at one or more recesses. The release function can preferably be arranged so that it is greater on or at the implant or implants fitted at the recess or recesses compared to the implant or implants arranged at a higher portion or higher portions of the jaw bone. In one embodiment, the release function is to be arranged to cause or bring about a level increase along the whole jaw bone. In an initial stage, the implant is covered with the jaw bone's soft tissue so that inner spaces are formed at each implant and at parts of the jaw bone and its soft tissue. A strengthening element can in this case be used in conjunction with the jaw bone and soft tissue, possibly with periosteum, so that no collapse takes place in the initial stage and the stage of incorporation. The strengthening elements (for example polymer membranes or membranes made of metal (titanium)) can be of a temporary or permanent nature and can in some cases be secured to the jaw bone by means of securing members, for example screws, etc. The strengthening element or strengthening elements can be provided with projecting parts via which each strengthening element can be anchored in the jaw bone, by means of screws for example.

Further embodiments are set out in the attached dependent claims.

By means of the invention, it is possible, in connection with the fitting of implants, to obtain high-quality new bone formations so that they permit a compensating effect, for example both in the horizontal plane of the jaw bone and in the vertical plane/vertical planes (on the outsides and/or insides of the jaw bone). The work can be carried out with essentially known means and techniques. GSS can be applied to implants with threads and/or outsides which have been provided with porous oxide layers with pores for storing GSS. The GSS forming the new bone structure can, if so desired, be combined with autologous bone, allogenic bone, xenografts and/or synthetic substances or materials available on the general market.

A presently proposed embodiment of an arrangement having the features characteristic of the invention will be described below with reference to the attached drawings, where FIG. 1 shows, in horizontal section, a lower jaw bone in which implants have been fitted and new bone formations have been initiated so that compensating effects in the horizontal plane of the jaw bone, i.e. the plane coinciding with the plane of the figure in FIG. 1, have been created, and where a strengthening element has been shown in connection with the implants and the jaw bone, FIG. 2 shows, in vertical section, implants arranged in or at irregularities in the jaw bone, one of the implants having been provided with a strengthening element, and the newly formed bone portions have created a level-compensating effect in the vertical direction or horizontal direction of the jaw bone, and FIG. 3 shows, in a diagrammatic side view, the new bone formation function having the effect of raising the level of the lower jaw.

In FIG. 1, a lower jaw bone is shown diagrammatically by 1. The lower jaw bone has defects or irregularities 2, 3, 4, 5, 6 along its side surfaces 1a, 1b extending substantially at right angles to the plane of the figure in FIG. 1 or inclined slightly from the bottom upward where they merge into the top surface 1c of the jaw bone 1. The main center line of the jaw bone is shown by 7. There is a need for implants to be able to be arranged substantially centrally around this center line, viewed in the horizontal plane according to FIG. 1. A first implant 8 has a vertical axis 8a which coincides with the arc-shaped line 7. A second implant 9 is arranged in the jaw bone such that its longitudinal axis extends substantially vertically through the center line 7. The implant 10 also has its vertical axis 10a arranged in said arc-shaped line 7. The implants can be arranged substantially vertically in the jaw bone or can slope slightly in the latter. The implants are arranged in formed/drilled jaw bone holes, the jaw bone holes for implants 9 and 10 being shown diagrammatically with reference numbers 1d and 1e. The optimum implant positioning in the jaw bone shown in FIG. 1 means that the implant 8a lies near the defect or irregularity 3. The implant 9 is arranged at the defects or irregularities 4 and 5. Similarly, the implant is arranged at the defects or irregularities 2 and 6. There is therefore a need to be able to form new bone at the defects/irregularities 2, 3, 4, 5 and 6. In accordance with the invention, new bone formations 11, 12, 13, 14 and 15 will be created so that the implants 8, 9 and 10 acquire the necessary or accepted embedding in newly formed bone and stability. In connection with the formation of new bone, spaces 17, 18, 19, 20 and 21 will be formed so that body fluids containing cells, for example stem cells, penetrate into each space from the jaw bone and possibly from its periosteum 21. In a first embodiment, said periosteum and the soft tissue of the jaw bone can stretch across the defects/irregularities to form the spaces 17, 18, 19, 20 and 21. Alternatively or in addition to this, strengthening elements, for example membranes 22, can be used. Said strengthening elements can be stiff and can be shaped or folded over the defects. Alternatively, they can be anchored to the side surface of the jaw bone by means of securing members/screws 23, 24. The strengthening element may possibly be provided with GSS 22a on the inner surface 22b. In the illustrative embodiment according to FIG. 1, the implants 9 and 10 have a degree of exposure to the spaces 19 and 21, which degree of exposure is shown by the angle .alpha., which can have values of up to 180 degree. for example. Each implant is provided with one or more concentrations of GSS, which concentration or concentrations has/have been shown by 25 in exaggerated thickness for reasons of clarity. The other implants too are provided with said concentrations or layers of GSS, and the concentration or layer on the implant 10 is indicated by 26. During the stage of incorporation or the new bone formation, body fluids can be secreted in accordance with the above and can penetrate into said spaces where at the same time GSS is released and interacts with the cells in the body fluids, and the formation of bone is thus effected in a manner known per se. In the illustrative embodiment according to FIG. 1, the implant 8 has been provided with a strengthening element which extends over the top surface of the implant. The strengthening element is indicated by 27 and in this case has projecting anchoring members 27a which extend radially outward, for example, from the center part of the strengthening element. The strengthening element can have two or more projecting portions and, in the illustrative embodiment shown in FIG. 1, it has four portions. At each projecting portion, the strengthening element can be screwed into the jaw bone with anchoring members/screws, for example screws 28, 29, the screw 28 having been screwed into the jaw bone in the direction toward its horizontal plane, and the screw 29 having been screwed in the direction toward a vertical plane of the jaw bone. The screw 29 is applied on the outer surface of the jaw bone. A tightening screw 30 for one portion is secured on the vertical inner surface of the jaw bone. As the new formation of bone by interaction between cells in secreted body fluid and released GSS can take place in a manner known per se, this will not be described in detail here. The implants can be made of titanium, ceramic, etc., and the strengthening elements can be made of durable material, for example polymer membrane, titanium, stainless steel, etc. The strengthening elements can be secured in a releasable or permanent manner. By means of the formation of new bone in said spaces, a considerably evened-out front surface 1a of the jaw bone is obtained, and this is also the case with the inner vertical surface 1b which is made even by means of the new bone formations 14 and 15. The implants can be threaded and can be of the self-tapping type. Alternatively, thread taps can be used to form the jaw bone holes 1d, 1e, into which the implants 8, 9 and 10 are thereafter screwed.

In accordance with FIG. 2, defects or irregularities 31, 32 and 33 may also be present in the vertical plane, i.e. coinciding with the plane of the paper in FIG. 2. There may be a requirement for implants 34, 35 to be able to be placed at the recesses 31 and 32. The implants 36, 37 are fitted at elevated parts 38, 39 along the jaw bone. The implants 36 and 37 therefore have a greater degree of recessing in the jaw bone than do the implants 34 and 35. Thus, for example, the implant has first portions 36a which are recessed in the jaw bone, and second portions 36b which are exposed from the jaw bone. The first portions can have a height H' which is, for example, 50-80% of the total height H of the implant. The height H" of the exposed portion 36b has a degree of exposure corresponding to said degree of recessing. The implant 34 has a first portion which has a height h' which is relatively small in relation to the total height h of the implant. The exposed part 346 has a height, h" which can be of prominent size. The first portion h' can have values of between 10 and 20% of the total height h. In accordance with the concept of the invention, the new bone formation 40, 41 will be arranged so that the function of new bone formation affords a leveling in the horizontal plane of the jaw bone, cf. the top surfaces 42 and 43 which adjoin the upper surfaces 44 and 45 of the top surface of the jaw bone structure. In this case too, the soft tissue 47, possibly with periosteum, can be used to create a space for the formation of new bone. A strengthening element 46 can be included or replace the soft tissue and periosteum function at the new bone formation 40, 41. The strengthening element is in this case provided with a top part 46a and with arm-shaped members 46b which extend away from said top part 46a. The implants 34, 35, 36 and 37 can be provided with different amounts of GSS or preferably different concentrations along the circumference and/or height. The principle is in this case such that the parts of the implant exposed in the initial stage bear a greater amount or greater concentration of GSS than those parts which extend within the jaw bone/the jaw bone hole. In the case of low degrees of recessing in the jaw bone for certain implants (cf. implants 34 and 35), said strengthening or fixing element 46 can be used to stabilize the implant during the stage of incorporation. The design of the strengthening element is dependent on the jaw bone structure, on the shape of the implant and on its extent within the jaw bone.

FIG. 3 shows an arrangement where a completely resorbed jaw bone 48 is to be provided with implants 49, 50, 51 and 52. On account of the resorption or the absence of jaw bone, it is necessary to obtain a level-raising effect by means of the above-indicated new formation of bone. The implants are initially anchored in the remaining jaw bone via their first portions (cf. above). The upwardly directed second portions can be covered with soft tissue, possibly with periosteum 53 and/or a strengthening element 54 which can serve as a stabilizing element for the implants during incorporation. By means of the arrangement shown, closed spaces 53, 54, 55, 56 and 57 are obtained. In accordance with the above, body fluid can be secreted from the jaw bone, and from the possibly used soft tissue and periosteum, and can penetrate into said spaces. In accordance with the above, the implants 47, 50, 51 and 52 are charged or provided with GSS which, when released from the implants, takes part in the interaction with the body fluids in order to form new bone. In accordance with FIG. 3, new bone 58, 59, 60 and 61 has formed in the spaces. The new bone formation preferably results in the level being raised along the entire extent of the jaw bone. The implants are fixed via the new bone formation and, after incorporation, acquire stable positions in the jaw bone. In some cases it may be desirable to complete the space between the implant and the bone/soft tissue with bone substitute, for example autologous bone, allogenic bone, xenografts and/or synthetic substances.

The invention is not limited to the embodiment shown above by way of example, and instead it can be modified within the scope of the attached patent claims and the inventive concept. The implants are used as supports for dental constructions, for example a bridge which has been symbolized by 62 in FIG. 2.

Reference may be made here to patent applications submitted to the Swedish patent office on the same day as the present patent application and by the same Applicant and inventor. Said applications have the following titles:

a) "Arrangement for using osteoinductive or bioactive material to induce bone and/or increase the stability of implants in the jaw bone, and an implant intended for this purpose".

b) "Arrangement for using bioactive or osteoinductive material to build up a bone-based lateral support for implants in the jaw bone".

"Arrangement for implants bearing growth-stimulating substance or substances, and one such implant".

d) "Arrangement for increasing the stress resistance of implants, and one such implant".

What is claimed is:

1. A method for using an arrangement for implanting into a jaw bone of a recipient, wherein said arrangement has two or more implants configured to be positioned at least partially into a hole disposed within the jaw bone, at least one strengthening element configured to be attached to the jaw bone, and at least one growth stimulating substance (GSS) disposed on the implants, wherein said method comprises:

providing a first implant and a second implant each having a first portion to be recessed in the jaw bone and a second portion to be exposed from the jaw bone, wherein at least said second portions bear the at least one GSS, and wherein the implants are provided with different amounts of GSS or different concentrations along the circumference and/or height;

forming a first hole and a second hole, wherein the first hole and second hole are dimensioned to receive the first implant and the second implant, respectively;

positioning the first implant into the first hole and the second implant into the second hole, wherein said second portions of the first implant and second implant bearing the at least one GSS extend outside the first hole and second hole, respectively;

attaching a strengthening element to the jaw bone, thereby defining a space between the strengthening element and the first implant and second implant, wherein said second portions bearing the at least one GSS are exposed to said space; and allowing the release of the GSS from said second portions of the first implant and second implant to form new bone growth into the defined space.

2. The method of claim 1, wherein said attaching a strengthening element to the jaw bone further comprises:
covering the first implant and second implant with one of at least a soft tissue of the jaw bone and a periosteum of the jaw bone.

3. The method of claim 1, wherein a first dimension is greater than a second dimension.

4. The method of claim 1, further comprises extending said first implant out of said first hole by a first dimension and extending said second implant out of said second hole wherein said first dimension is greater than a second dimension.

5. The method of claim 1, wherein said strengthening element is configured to interface with a dental structure positioned adjacent to said strengthening element.

6. The method of claim 1, which comprises screwing said strengthening element to the jaw bone with one or more screws in the direction towards a horizontal plane of the jaw bone and with one or more screws in the direction towards a vertical plane of the jaw bone.

7. The method of claim 1, which comprises anchoring said strengthening element to the jaw bone with one or more arm-shaped members extending from said strengthening element.

8. The method of claim 1, wherein said strengthening element is extended over one of at least a top face of the jaw bone and a vertical side of the jaw bone.

9. The method of claim 1, wherein said strengthening element is extended over a vertical side of the jaw bone.

10. The method of claim 1, wherein the parts of the implants exposed to the space bear a greater amount or greater concentration of GSS than those parts which extend within the jaw bone/the jaw bone holes.

* * * * *